United States Patent [19]

Blom et al.

[11] 4,435,853
[45] Mar. 13, 1984

[54] VOICE PROSTHESIS DEVICE AND PLACEMENT TOOL THEREFOR

[75] Inventors: Eric D. Blom; Mark I. Singer, both of Indianapolis, Ind.

[73] Assignee: Hansa Medical Products, Inc., Indianapolis, Ind.

[21] Appl. No.: 373,635

[22] Filed: Apr. 30, 1982

[51] Int. Cl.³ .................. A61F 1/20; A61B 17/00
[52] U.S. Cl. .................... 3/1.3; 128/207.16;
128/207.17; 128/303 R
[58] Field of Search .......... 3/1.3; 128/207.14, 207.15,
128/207.16, 207.17, 303 R; 179/1 AL

[56] References Cited

U.S. PATENT DOCUMENTS

| | | | |
|---|---|---|---|
| 3,137,299 | 6/1964 | Tabor | 128/207.16 |
| 3,169,529 | 2/1965 | Koenig | 128/207.14 |
| 3,499,450 | 3/1970 | Rathjen | 128/207.17 |
| 3,747,127 | 7/1973 | Taub | 3/1.3 |
| 3,844,290 | 10/1974 | Birch et al. | 128/207.16 |
| 3,952,335 | 4/1976 | Sorce et al. | 3/1.3 |
| 4,044,402 | 8/1977 | Edwards | 3/1.3 |
| 4,269,184 | 5/1981 | Montgomery | 128/207.14 |
| 4,274,162 | 6/1981 | Joy et al. | 3/1.3 |
| 4,325,366 | 4/1982 | Tabor | 128/207.16 |

FOREIGN PATENT DOCUMENTS 2077109 12/1981 United Kingdom ............ 3/1.3

OTHER PUBLICATIONS

"An Endoscopic Technique for Restoration of Voice After Laryngectomy" by M. I. Singer et al., Reprint from Annals of Otology, Rhinology and Laryngology, vol. 89, No. 6, Nov.-Dec. 1980, pp. 529-533.

*Primary Examiner*—Ronald L. Frinks
*Attorney, Agent, or Firm*—Barnes & Thornburg

[57] ABSTRACT

A low pressure prosthesis device includes a cylindrical housing having a proximal end with strap elements extending outwardly from the proximal end, a distal end and a port operatively cooperating with a tracheostoma in the neck of a patient. The cylindrical housing further includes a one-way valve structure comprised of an annular sealing rim positioned perpendicularly in the housing adjacent the distal end and a valve membrane hingedly mounted within the housing to cooperate with the annular sealing rim to provide the one-way valve structure. An annular collar flange extends outwardly from the housing and is positioned to abut against the esophagus tissue when the device has been positioned within a fistula connecting the esophagus to the tracheostoma. The valve membrane is movable from the closed to the opened position when air passes through the port from the tracheostoma to the esophagus to produce alaryngeal speech and sounds in the patient.

8 Claims, 5 Drawing Figures

VOICE PROSTHESIS DEVICE AND PLACEMENT TOOL THEREFOR

BACKGROUND OF THE INVENTION

The present invention relates to a novel voice prosthesis device which is insertable through a fistula to connect and channel air directly from the lungs through the trachea to the esophagus for voice restoration after a total laryngectomy.

In the past, voice prosthesis devices have been suggested for insertion into a fistula to connect the tracheostoma with the esophagus to channel air from the lungs to the esophagus to permit alaryngeal speech by the patient or user. One such voice prosthesis device is disclosed in our co-pending application Ser. No. 316,055, filed on Oct. 29, 1981, and entitled "Method and Apparatus for a Tracheal Valve", and in a paper entitled "An Endoscopic Technique For Restoration of Voice After Laryngectomy", *Annals of Otology, Rhinology and Laryngology,* 1980, Vol. 89, No. 6. However, the elongated hollow tube or duck-bill type valve slit in the elongated hollow tube requires approximately 90 centimeters of water pressure before the duck-bill type valve opens to permit air to enter the esophagus for speaking. Additionally, a voice prosthesis device, known as the Panje device, is a shorted criss-crossed slitted duck-bill device, which includes self-retaining flanges which abut against each side of the tracheoesophageal wall to hold the device in the fistula. However, the Panje type device requires approximately 400 centimeters of water pressure before voice sounds are achieved, a pressure which is totally unsatisfactory for most, if not all, patients or users. Because a normal larynx requires approximately 35 centimeters of water pressure for speech, it can be seen that a voice prosthesis device, which closely approximates normal voice pressure, is highly desirable and has been unattained by the duck-bill type prior art devices.

Additionally, U.S. Pat. No. 3,747,127 discloses a fistula valve FA which is merely a check valve mounted on the outside of the exterior proximal end of a tubular extension. Because the valve opens and closes from the top of the proximal end and is unprotected because it is not in a recessed position within the tube, such a structure is unsatisfactory in communicating between the trachea and the esophagus because the valve is readily exposed to the esophageal contents, and liquids and matter therein may penetrate the valve from the esophagus with resultant aspiration into the lungs of the user or patient. Accordingly, such devices have found no limited application in restoring speech to patients having a total laryngectomy.

SUMMARY OF THE INVENTION

It is an object of the present invention to provide a low pressure voice prosthesis device which includes valve means positioned therein which approximates the pressure required for normal speech.

It is another object of the present invention to provide a voice prosthesis device with a low pressure valvular design that is internalized in the distal end of the prosthesis device to protect the valve opening and closing excursion from becoming impeded by tissue or esophageal contents.

It is a further object of the present invention to provide a novel voice prosthesis device which is reliable in operation and which is a miniature one-way valved tube readily positioned in a patient having a total laryngectomy and subsequent tracheoesophageal fistula.

It is still another object of the present invention to provide a novel tool structure for positioning the low pressure voice prosthesis device into the prescribed position in a patient.

The voice prosthesis device in accordance with the present invention is useful in insertion into a fistula to direct or channel pulmonary air from the tracheostoma into the esophagus of a patient to produce alaryngeal speech. The voice prosthesis device includes an elongated tubular housing which is constructed and composed of a medical grade silicone material having a proximal end or tracheal end and a distal or esophageal end. Attached to the proximal end are beveled straps or flanges which aid and assist as retention flanges in maintaining the voice prosthesis device in the fistula between the tracheostoma and esophagus. The elongated tubular housing includes a beveled extension on the distal end thereof which extends into the esophagus to prevent liquid and other matter from penetrating the one way valve which is positioned intermediate the distal and proximal ends of the cylindrical housing, as will hereinafter be described.

The cylindrical housing includes a port therein adjacent the proximal end on the inferior surface thereof which permits expelled air from the tracheostoma to enter the voice prosthesis device and pass through the one-way valve into the esophagus to produce alaryngeal speech in the patient. The one-way valve structure, positioned within the voice prosthesis device, is comprised of a substantially perpendicular mounted valve membrane hinged on the interior side of the cylindrical housing and adjacent to an annular rim or valve sealing structure mounted within the cylindrical housing to provide a hinged valve which permits the passage of air from the trachea into the esophagus. It is preferred that the valve membrane be mounted and hinged on the inferior or lower portion or side of the cylindrical housing and that the valve structure be opened and closed by a pressure comparable to the pressure necessary to operate a normal larynx, or approximately about 35 centimeters of water pressure.

Additionally, the cylindrical housing of the prosthesis device includes an annular flange or retention collar positioned therearound, preferably located between the one-way valve structure within the annular housing and the port on the inferior surface of the housing. The annular flange structure aids in obtaining a seal when the voice prosthesis device is inserted through the fistula and abuts the esophageal surfaces of the tracheoesophageal wall to retain and hold the voice prosthesis device in position.

The novel voice prosthesis and one-way valve structure therein in accordance with the present invention provides a low pressure voice prosthesis device whose operative pressure closely approximates the pressure necessary to operate a normal individual's larynx. Such a reduction in pressure necessary to move the one-way valve from the closed to the open position greatly reduces the strain upon the patient in producing alaryngeal speech and permits the patient to produce alaryngeal speech and sounds similar to those produced by the patient's former larynx. Moreover, it has been found that when the one-way valve membrane is in the closed position, during normal swallowing the positive pressure gradient within the esophagus further seats the valve membrane to its closed position to enhance its effectiveness as a one-way valve. Additionally, the beveled extension on the distal end of the cylindrical housing acts as a hood over the valve to shelter it from fluid and other matter that is swallowed through the esophagus. This permits an increased wearing time by the patient of the novel voice prosthesis device in accordance with the present invention. Also, the annular flange or retention collar provides a locking action when the retention collar is inserted through the fistula to abut against the esophageal side of the tracheoesophageal wall to hold and retain the novel prosthesis device in position. This locking action provided by the retention collar, together with the beveled stays on the distal end of the cylindrical housing, insures the device will not become dislodged during usage by a patient.

DETAILED DESCRIPTION

Figure 1:
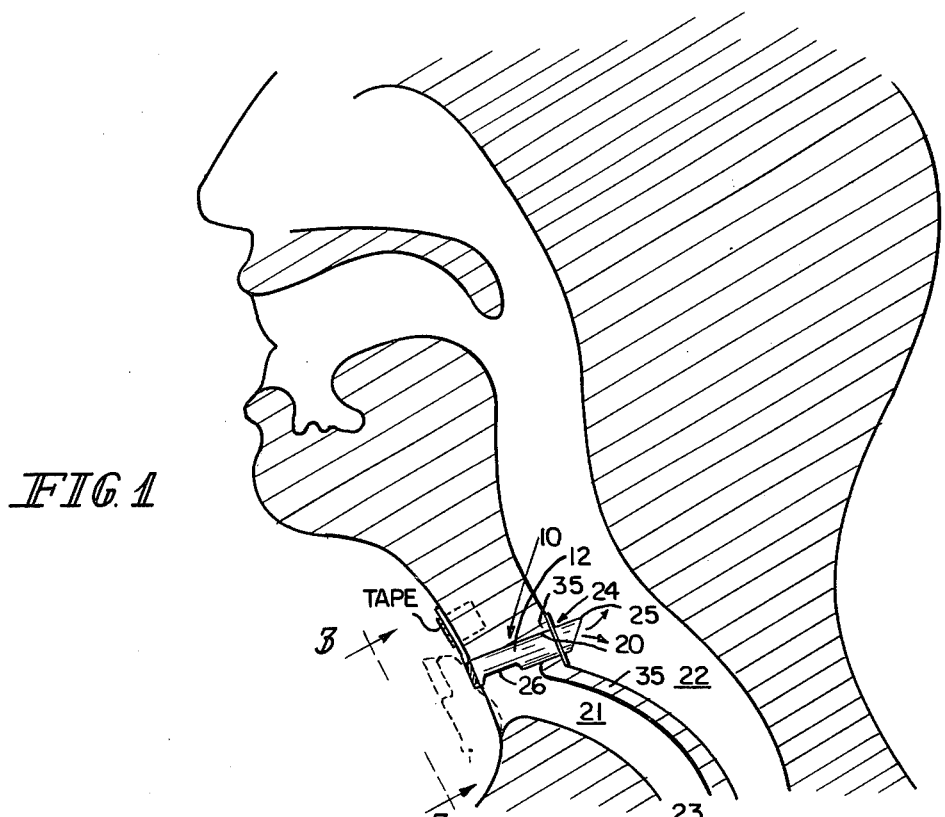
FIG. 1 is a schematic view showing the installation in a patient of the voice prosthesis device in accordance with the present invention.

Referring now to the drawings wherein like numerals have been used throughout the several views to designate the same or similar parts, FIG. 1 shows the voice prosthesis device 10 in accordance with the present invention positioned in a patient having a total laryngectomy.

Figure 2:
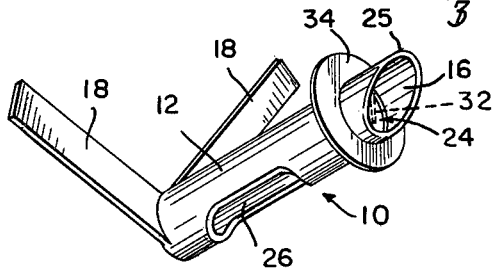
FIG. 2 is a perspective view of the voice prosthesis device in accordance with the present invention.
Figure 3:
FIG. 3 is an end view taken along lines 3—3 of FIG. 1.
Figure 4:
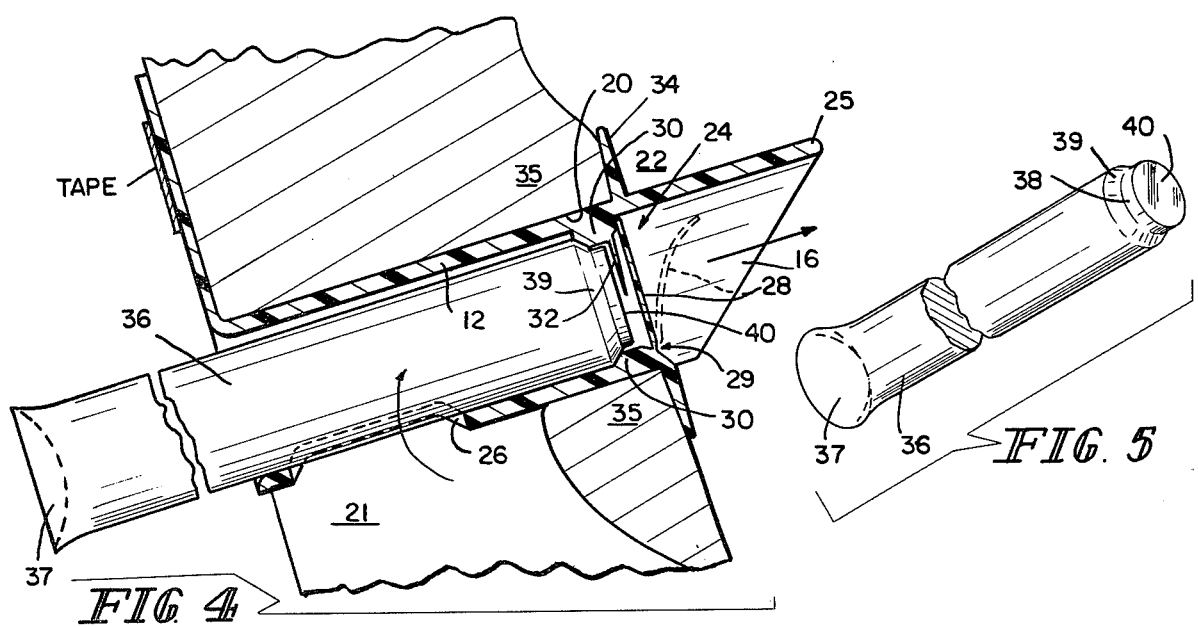
FIG. 4 is an enlarged view showing the passage of air through the one-way valve structure of the voice prosthesis device in accordance with the present invention.

As shown in FIGS. 2-4, the voice prosthesis device 10 includes an elongated tubular housing 12 which is constructed and composed of a medical grade silicone material having a proximal or tracheal end 14 and a distal or esophageal end 16. Mounted to the proximal end 14 are beveled straps or flanges 18 (FIGS. 2 and 3) which may be taped to the neck of the patient (FIG. 1) to assist in retaining and maintaining the voice prosthesis device 10 in a fistula 20, which is a surgical connection between the tracheostoma 21 and the esophagus 22 of the patient. The elongated tubular housing 12 includes an beveled extension member 25 on the distal end 16 which extends into the esophagus 22 and which prevents esophageal fluids and other matter from penetrating the tubular housing and the one-way valve means 24 which is positioned within the tubular housing and adjacent the distal end 16 of the cylindrical housing, as will hereinafter be described.

The cylindrical housing 12 includes also a port 26 therein intermediate between the proximal end 14 and the one-way valve means which permits expelled air from the tracheostoma 21 and the trachea 23 to enter the tubular housing 12 of the voice prosthesis device and pass through the one-way valve means 24 into the esophagus 22 to produce alaryngeal speech in the patient.

The one-way valve means 24 is positioned within the tubular housing and includes a substantially perpendicular mounted valve membrane 28 (FIG. 4) hinged 39 on the interior side of the cylindrical housing and adjacent to an annular rim or valve sealing structure 30 (FIG. 4) mounted within the cylindrical housing 12. The annular valve sealing structure 30 cooperates with the hinged valve membrane 28 to selectively permit the passage or channeling of air from the trachea 23 into the esophagus 22, as will hereinafter be described. It is preferred that the valve membrane 28 is mounted and hinged 29 on the interior side of the valve membrane 28 on the bottom thereof and that the valve membrane is opened and closed by a pressure comparable to that necessary to operate a normal larynx, or approximately 35 centimeters of water pressure. Also, it is preferred that a projection element 32 (FIG. 4) extend downwardly from the interior of the annular rim or valve sealing structure 30 towards the center of the cylindrical housing, which projection prevents the pressure sensitive valve membrane 28 from overlapping the annular rim or sealing structure when the voice prosthesis device 10 is inserted through a fistula to connect the esophagus and the tracheostoma or inadvertently during cleaning of the prosthesis device 10.

The cylindrical housing 12 further includes an annular flange or retention collar 34 positioned therearound. The retention collar 34 is preferably positioned on the cylindrical housing between the one-way valve means 24 and the port 26, on the inferior surface of the housing. The retention collar 34 aids in obtaining a seal when the voice prosthesis device is inserted through the fistula because the retention collar abuts and engages the esophageal side of the tracheoesophageal wall 35 to retain and hold the prosthesis device in position. During insertion of the device through a fistula, it has been observed that the retention collar snaps into a substantially annular planar position against the esophageal tissues when the device has been properly positioned in the patient. When in such a position, the device is firmly retained in position and will not become dislodged.

Figure 5:
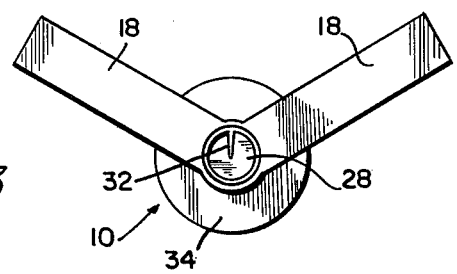
FIG. 5 is a perspective view of the placement tool for positioning the voice prosthesis device in accordance with the present invention in a patient.

In FIG. 5, a placement tool 36 is shown which is particular useful in engaging the voice prosthesis device 10 when the device is positioned through the fistula 20 to connect the esophagus and the tracheostoma. The placement tool 36 preferably includes an enlarged gripping or handle end 37 adapted to receive a finger or thumb of the patient and a placement end 38. The placement end 38 includes a projection 40 thereon, the shoulder 39 of which is adapted to cooperate with and engage the annular rim or valve sealing structure 30, as will hereinafter be described. When the placement tool is inserted into the elongated tubular housing 12, the shoulder 39 on the placement end 38 engages the annular rim and valve sealing structure 30 to position the device in the fistula to connect the esophagus and trachea. However, the projection 40 does not engage or disturb the sensitive valve membrane 28 of the one-way valve means 24 during this operation, as shown in FIG. 4. Thus, during insertion of the voice prosthesis device into the fistula, the patient is insured that the valve membrane 28 will be in aligned relation with respect to the annular sealing structure 30 and will be in operative condition.

It is preferred that a projection 32 extend inwardly from the annular rim or valve sealing structure 30 towards the center of the housing. The projection prevents the valve membrane 28 from overlapping the annular rim during usage of the prosthesis device, cleaning, and placement of the device into the fistula connecting the esophagus and the tracheostoma. During this placement procedure, the tendency of voice prosthesis devices is to collapse and be squeezed together and, accordingly, the projection 32 helps to prevent the valve membrane 28 from overlapping the annular sealing rim and becoming inoperative. To prevent the squeezing of the valve means 24 during insertion, the placement tool 36, when positioned within the distal end 14 of the tubular housing 12, insures that the one-way valve means 24 is maintained in proper aligned position to provide the unique low pressure operation of the voice prosthesis device.

The unique voice prosthesis device and one-way valve means mounted therein in accordance with the present invention provides a low pressure voice prosthesis device whose operative pressure closely approximates the pressure required to operate the normal larynx of an individual and has particular application and use in conjunction with the tracheal valve disclosed in our co-pending application Ser. No. 316,055. It has been observed that the average pressure necessary to operate a normal larynx is about 35 centimeters of water and initial observation of the present invention indicates that a range of about that pressure or less readily moves the valve membrane from the closed to the open position. However, it is understood that the scope of the present invention is not limited to a specific pressure range because of the novelty of the unique one-way valve structure positioned within the tubular housing of the prosthesis device. Such a reduction in the pressure necessary to move the one-way valve membrane from the closed to the open position greatly reduces the strain upon the patient in producing alaryngeal speech and sounds similar to those produced by the patient's former larynx. Alaryngeal speech occurs when a finger (as shown in dotted lines) covers the opening to the tracheostoma 21 and air is directed through port 26 and into the esophagus 22. Additionally, as shown in FIG. 4, it has been found that when the one-way valve membrane is in the closed position, normal swallowing by the patient will further seat the valve membrane to insure an effective one-way valve in the closed position.

Also, the positioning of the one-way valve means 24 at or adjacent the distal end 16 of the tubular housing 12 and the cooperation with the beveled extension member 25 thereon, protects the valve membrane during its opening and closing excursion or movement from esophageal fluids and other matter. Thus, the beveled extension member 25 acts as an umbrella or shield which prevents esophageal fluids or swallowed matter from becoming impeded.

While a preferred embodiment of the voice prosthesis device and inserter tool have been shown and described above, person's skilled in the art will readily appreciate the various changes and modifications that may be made without departing from the spirit and scope of the present invention, which is defined in the following claims.

We claim:

1. A voice prosthesis device for placement in a fistula to channel air from a tracheostoma to the esophagus including in combination:
   a cylindrical housing having a proximal end with strap means extending outwardly therefrom, a distal end, a port therein operatively cooperating with the tracheostoma, with said distal end having a beveled extension integral therewith,
   one-way valve means including an annular sealing rim positioned perpendicularly within said housing adjacent said distal end and a valve membrane hingedly mounted to said housing on the side thereof adjacent said distal end of said housing to cooperate with said annular sealing rim, and
   an annular collar means extending outwardly from said housing, said annular collar means adapted to abut against the esophagus tissue when the device has been positioned in the fistula, to retain and hold the device in proper position, such that upon covering the tracheostoma opening, said valve membrane is moved by the channeled air from the closed position against said annular sealing rim to an open position wherein the channeled air enters the esophagus to produce alaryngeal speech by the patient.

2. The voice prosthesis device in accordance with claim 1 wherein said annular sealing rim of said valve means further includes a projection extending inwardly toward the center of said housing, said projection cooperating with said valve membrane to maintain the same in alignment against said annular sealing rim when said valve membrane is moved from said open to said closed position.

3. The voice prosthesis device in accordance with claim 1 wherein said annular collar means is positioned on said cylindrical housing between said port and said valve means.

4. The voice prosthesis device in accordance with claim 1 wherein said valve membrane in said housing is hingedly mounted on the interior thereof for cooperating with said annular sealing rim when in the closed position to seal the same.

5. The voice prosthesis device in accordance with claim 1 wherein about 35 centimeters of water pressure is sufficient to move said valve membrane from said closed to said open position and thereby permit channeled air to pass into the esophagus to produce alaryngeal speech by the patient.

6. The voice prosthesis device in accordance with claim 1 wherein said cylindrical housing is comprised of medical grade silicone.

7. The voice prosthesis device in accordance with claim 1 wherein said one-way valve means is substantially perpendicularly positioned within said cylindrical housing adjacent to said distal end where said beveled extension is integral therewith, with said beveled extension providing a shield to prevent esophageal matter from impeding the movement of said valve membrane between said closed and said open position.

8. A placement tool for positioning a voice prosthesis device into a fistula connecting the tracheostoma with the esophagus of the patient, the voice prosthesis device having a cylindrical housing with a one-way valve membrane and an annular sealing rim positioned perpendicularly within the housing, said placement tool including in combination an elongated housing member having a handle portion on one end thereof and a placement portion on the end opposite said handle portion, said placement portion having a shoulder thereon which shoulder engages the annular sealing rim positioned within the housing when the tool is inserted within the cylindrical housing to position the voice prosthesis device within the patient, with said placement portion further including a projecting portion extending beyond said shoulder portion which cooperates with the valve membrane to maintain the valve membrane in perpendicular relationship with respect to the annular sealing rim.

* * * * *